United States Patent
Ohya

(10) Patent No.: US 7,974,936 B2
(45) Date of Patent: Jul. 5, 2011

(54) STRUCTURAL FORMULA DISPLAY SYSTEM, METHOD, AND PROGRAM STORAGE MEDIUM STORING PROGRAM THEREOF

(75) Inventor: Tomohiro Ohya, Fukuoka (JP)

(73) Assignee: Fujitsu Limited, Kawasaki (JP)

( * ) Notice: Subject to any disclaimer, the term of this patent is extended or adjusted under 35 U.S.C. 154(b) by 746 days.

(21) Appl. No.: 12/001,313

(22) Filed: Dec. 11, 2007

(65) Prior Publication Data

US 2008/0201347 A1  Aug. 21, 2008

(30) Foreign Application Priority Data

Feb. 15, 2007  (JP) ................. 2007-034636

(51) Int. Cl.
  G06F 17/21 (2006.01)
  G06F 17/22 (2006.01)
  G09G 5/22 (2006.01)
  G06G 7/58 (2006.01)
(52) U.S. Cl. ............. 706/13; 706/46; 706/48; 345/689; 703/12
(58) Field of Classification Search .............. 706/13
  See application file for complete search history.

(56) References Cited

FOREIGN PATENT DOCUMENTS
JP  A 4-127380  4/1992

OTHER PUBLICATIONS

Weininger, Smiles, a Chemical Language and Information System. 1. Introduction to Methodology and Encoding Rules, American Chemical Society, 1988, pp. 31-36.*
Barker, "Syntactic definition and parsing of molecular formulae: Part 1 Initial syntax definition and parse implementation", 1974.*
Weininger, "SMILES, a Chemical Language and Information System. 1. Introduction to Methodology and Encoding Rules", American Chemical Society, 1988.*

* cited by examiner

Primary Examiner — Jeffrey A Gaffin
Assistant Examiner — Nathan H Brown, Jr.
(74) Attorney, Agent, or Firm — Greer, Burns & Crain, Ltd.

(57) ABSTRACT

Character string divider divides a targeted character string into a plurality of groups at each bonding sites on a main chain. In the character string dividing process, the character string divider adds starting/ending symbols to the targeted character string, inserts a delimiter between adjacent characters, changes a notation related to oxo acids, reconstructs an atomic symbol consisting of two characters, changes a notation regarding a subscript or superscript, links hydrogen to another element, reconstructs a set of side chains, reconstructs a character string consisting of one group, reconstructs a back-end group, reconstructs a double bond in a group, and removes the starting/ending symbols. Character string reverser reverses the alignment of the groups.

6 Claims, 15 Drawing Sheets

CH₂OCOCH₃ ⇨ %CH₂OCOCH₃$ ~202

CH₃COOCH₂ ⇨ $CH₃COOCH₂% ~204

FIG. 7

%CH₂OCOCH₃$ ⇨ %/C/H/2/O/C/O/C/H/3/$ ~206

\*: CHARACTER STRING
?: ROMAN LETTER OTHER THAN "O"
l: LOWER-CASE ROMAN LETTER
n: NUMBER, n≧3
n̲: NUMBER, n̲=n−1

FIG. 9

/l → l  ~222    l: LOWER-CASE ROMAN LETTER

FIG. 10

/n → n  ~224
/"+" → "+"  ~226
/"−" → "−"  ~228
n/ → n  ~230 n: NUMBER

\* : CHARACTER STRING
\*̲ : \* WITHOUT DELIMITERS

?: ROMAN LETTER OTHER THAN "H", "D"
m: NUMBER, m≧2
n: NUMBER, n≧2

FIG. 14

"CH"/"O"/$ → "HCO"/$ ~262
"CD"/"O"/$ → "DCO"/$ ~264
$/"H"/"C"/"O" → $/"CHO" ~266
$/"D"/"C"/"O" → $/"CDO" ~268
"N"/"O₂"/$ → "O₂N"/$ ~270
$/"O₂"/"N" → $/"NO₂" ~272
"OH"/$ → "HO"/$ ~274
"OD"/$ → "DO"/$ ~276
$/"H"/"O" → $/"OH" ~278
$/"D"/"O" → $/"OD" ~280

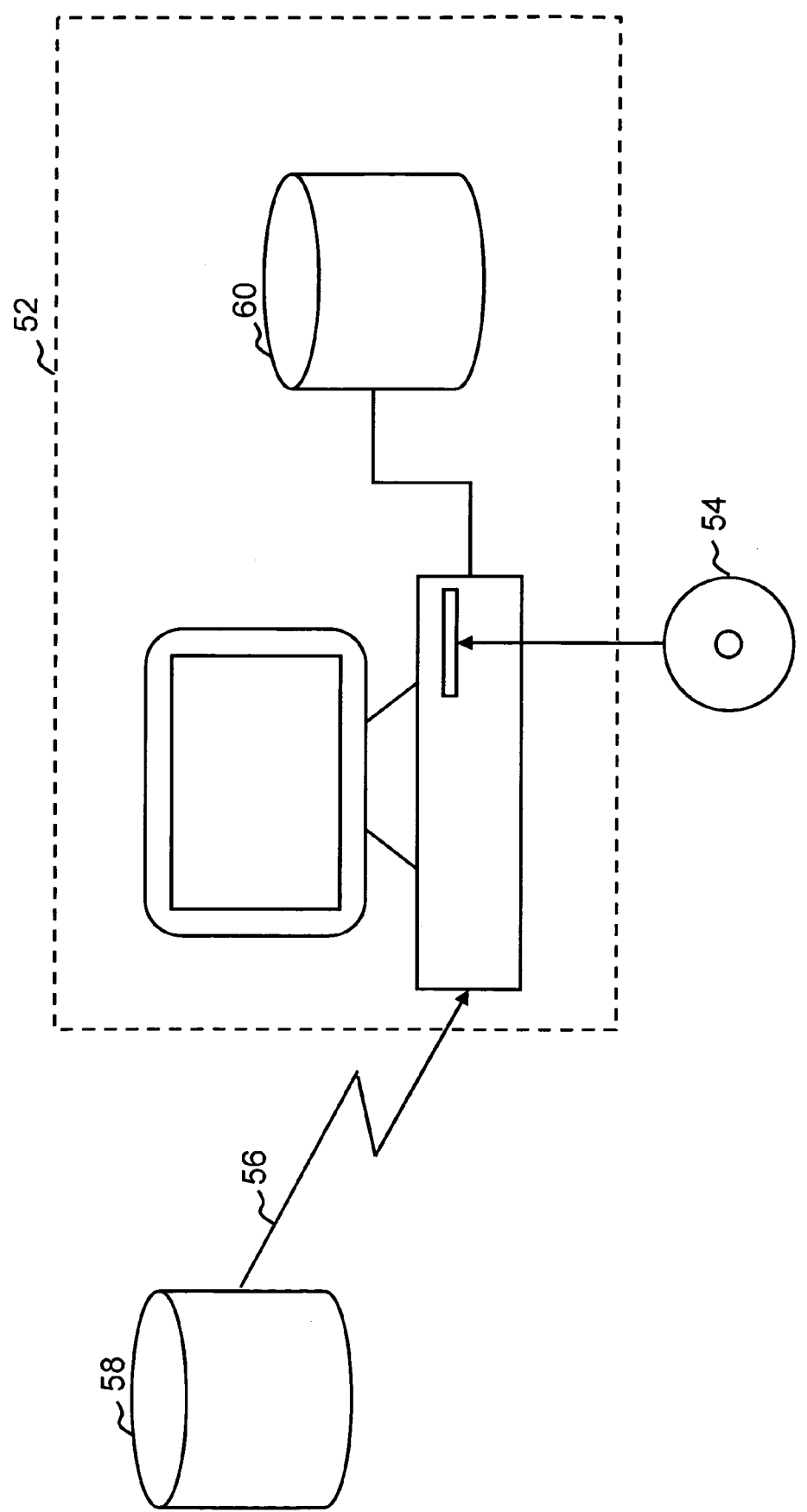

STRUCTURAL FORMULA DISPLAY SYSTEM, METHOD, AND PROGRAM STORAGE MEDIUM STORING PROGRAM THEREOF

BACKGROUND OF THE INVENTION

1. Field of the Invention

The present invention relates to a system which displays structural formulae of compounds, and more particularly, relates to a method for displaying a character string as a part of a structural formula.

2. Description of the Related Art

Systems for displaying structural formulae of compounds have been devised so that researchers who study compounds can easily handle compound data (for example, refer to Japanese Patent No. 2620402).

FIG. 1 is a diagram illustrating examples of screen images displaying a structural formula of a compound. The methods for displaying a structural formula of a compound include a method wherein the structural formula is shown as a graphic in which individual elements constituting the compound are linked together by lines representing chemical bonds (e.g., Structural Formula 102), a method wherein the structural formula is shown as a character string in which groups (each group including one or more atoms joined together) constituting the compound are linked together (e.g., Structural Formula 104), and a method wherein a part of the structure of the compound is shown as a graphic and another part of the compound is shown as a character string (e.g., Structural Formula 106).

In Structural Formula 106, the character string part is arranged on the right side of the graphic part. Here, consideration is given for the case where the positions of the character string part and the graphic part are reversed.

FIG. 2 is a diagram illustrating an example of change in expression of a character string part following change in position of the character string part according to a conventional method. In Structural Formula 112, the character string part in Structural Formula 106 is moved as it is to the left side of the graphic part. In Structural Formula 106, the group bonded to the benzene ring is "CH2". However, in Structural Formula 112, the group bonded to the benzene ring appears to be "CH3", and thus, Structural Formula 112 is inconvenient. Consequently, to date, the left-to-right order in alignment of atom symbols in the character string part has been reversed as in Structural Formula 114. Hereinafter, such reversal operation of the left-to-right order in alignment is referred to as "mirror-reverse".

While the group bonded to the benzene ring is "CH2" when the structural formula is displayed as in Structural Formula 114, it is difficult for the user to understand at a glance the structure of the compound in Structural Formula 114, since the alignment of atom symbols in the character string part is different from the typical alignment.

SUMMARY OF THE INVENTION

It is an object of the present invention to provide a structural formula display method in which the structure of a compound can be easily understood by the user even if the alignment of elements in a character string part is changed following the movement of the character string part in a structural formula.

According to a first aspect of the present invention, there is provided a structural formula display system which displays a structural formula of a compound. The structural formula display system includes: an input unit which accepts the structural formula; a character string divider which divides a character string which corresponds to a part of the structural formula into a plurality of substrings, wherein each of said substrings corresponds to a group which is derived by dividing the part of the structural formula at each bonding site on a main chain; an alignment reverser which reverses an order of alignment of the plurality of substrings in the character string; and an output unit which displays the structural formula after the reversal.

The character string divider of the structural formula display system may modify a substring out of the plurality of substrings.

According to a second aspect of the present invention, there is provided a structural formula display method which is performed by a structural formula display system which displays a structural formula of a compound. The structural formula display method includes the steps of: accepting the structural formula; dividing a character string which corresponds to a part of the structural formula into a plurality of substrings, wherein each of the substrings corresponds to a group which is derived by dividing the part of the structural formula at each bonding site on a main chain; reversing an order of alignment of the plurality of substrings in the character string; and displaying the structural formula after the reversal.

According to a third aspect of the present invention, there is provided a program storage medium which is readable by a computer and stores a program of instructions for the computer for executing a structural formula display method to display a structural formula of a compound. The structural formula display method includes the steps of accepting the structural formula; dividing a character string which corresponds to a part of the structural formula into a plurality of substrings, wherein each of the substrings corresponds to a group which is derived by dividing the part of the structural formula at each bonding site on a main chain; reversing an order of alignment of the plurality of substrings in the character string; and displaying the structural formula after the reversal.

According to the present invention, in the structural formula display system, even if the alignment of elements in the character string is changed, the expression of each group is maintained familiar to the user. Thus, it is possible to provide a structural formula display method in which the structure of the compound can be easily understood by the user.

BRIEF DESCRIPTION OF THE DRAWINGS

FIG. 7 is a diagram illustrating examples of addition of starting/ending symbols;

FIG. 8 is a diagram illustrating an example of insertion of delimiters;

FIG. 9 is a diagram illustrating examples of the substitution rule regarding oxo acids;

FIG. 10 is a diagram illustrating an example of the substitution rule for reconstructing an atomic symbol consisting of two characters;

FIG. 11 is a diagram illustrating examples of the substitution rule regarding a subscript or superscript;

FIG. 12 is a diagram illustrating examples of the substitution rule regarding hydrogen;

FIG. 13 is a diagram illustrating an example of the substitution rule for reconstructing a set of side chains FIG. 14 is a diagram illustrating examples of the substitution rule for reconstructing a character string consisting of one group;

FIG. 15 is a diagram illustrating examples of the substitution rule for reconstructing a back-end group;

FIG. 16 is a diagram illustrating examples of the substitution rule for reconstructing a double bond in a group;

FIG. 18 is a diagram illustrating an example of a computer environment.

DESCRIPTION OF THE PREFERRED EMBODIMENTS

Embodiments of the present invention will now be described with reference to the drawings. In the following, a substring corresponding to a group is also referred to as a group for the sake of convenience. In the same way, an atomic symbol of an element is also referred to as an element, an atomic symbol of a specific element is referred to the name of the specific element, and so forth.

Figure 1:
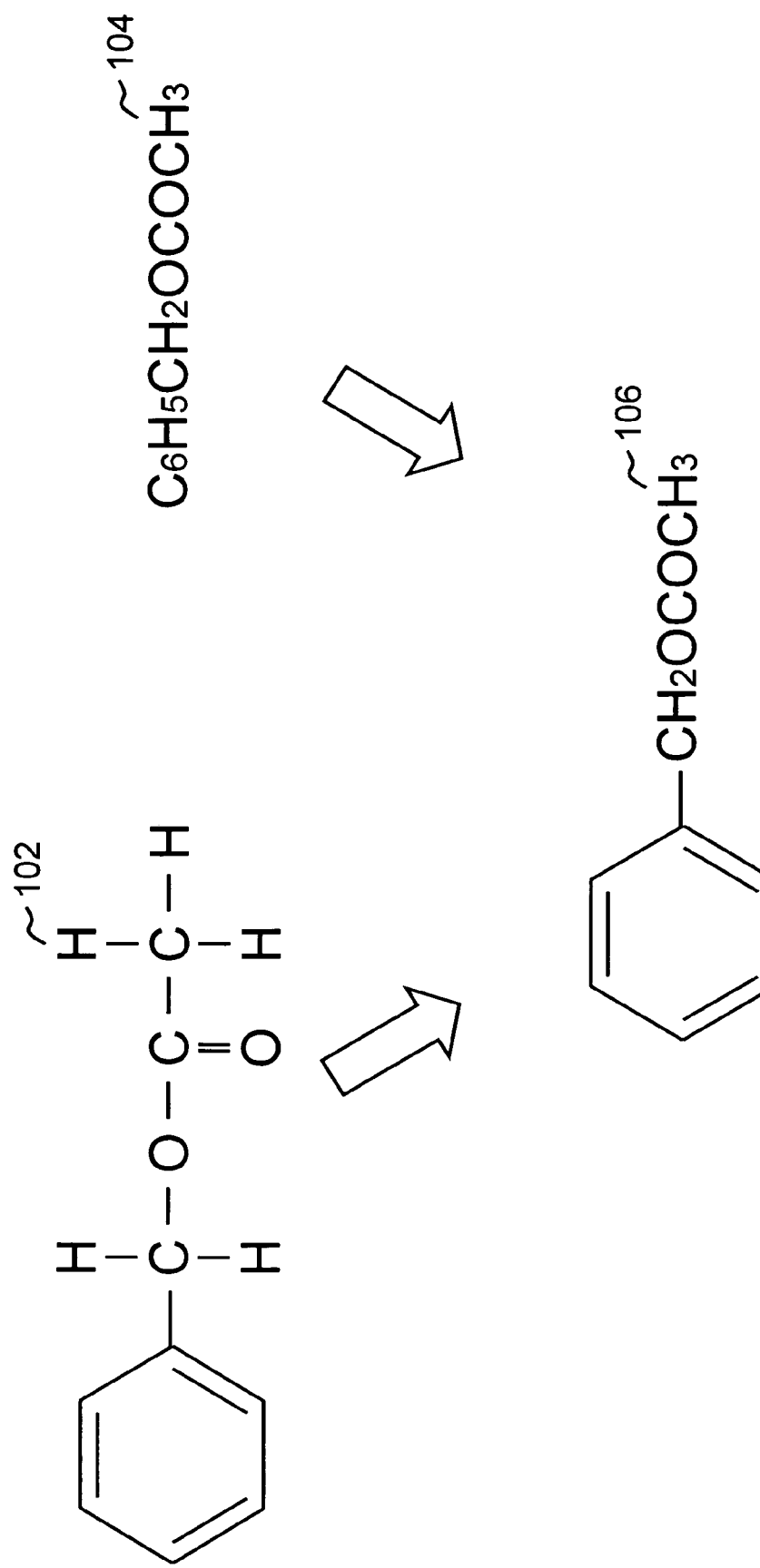
FIG. 1 is a diagram illustrating examples of screen images displaying a structural formula of a compound.
Figure 2:
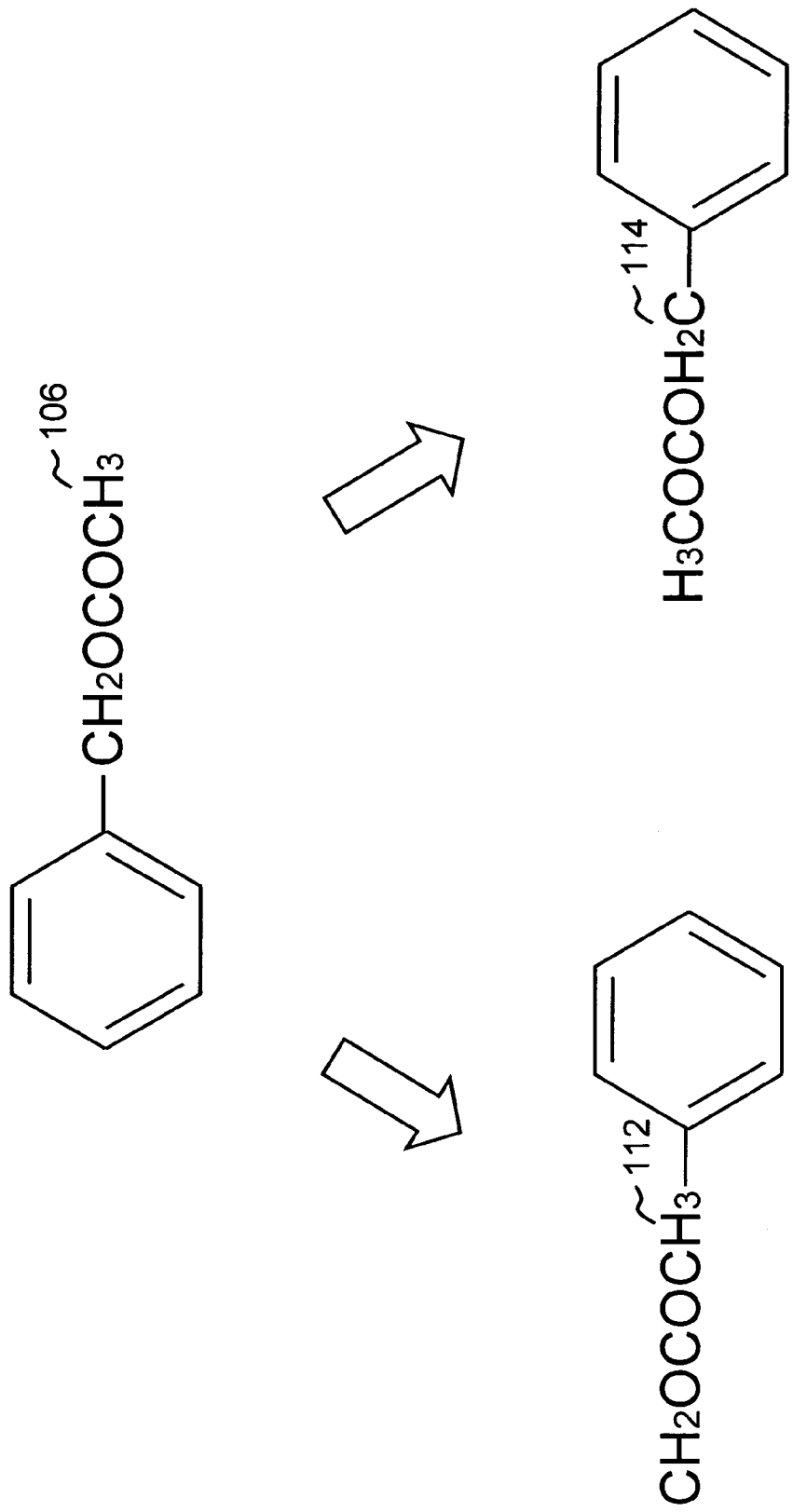
FIG. 2 is a diagram illustrating an example of change in expression of a character string part following change in position of the character string part according to a conventional method.
Figure 3:
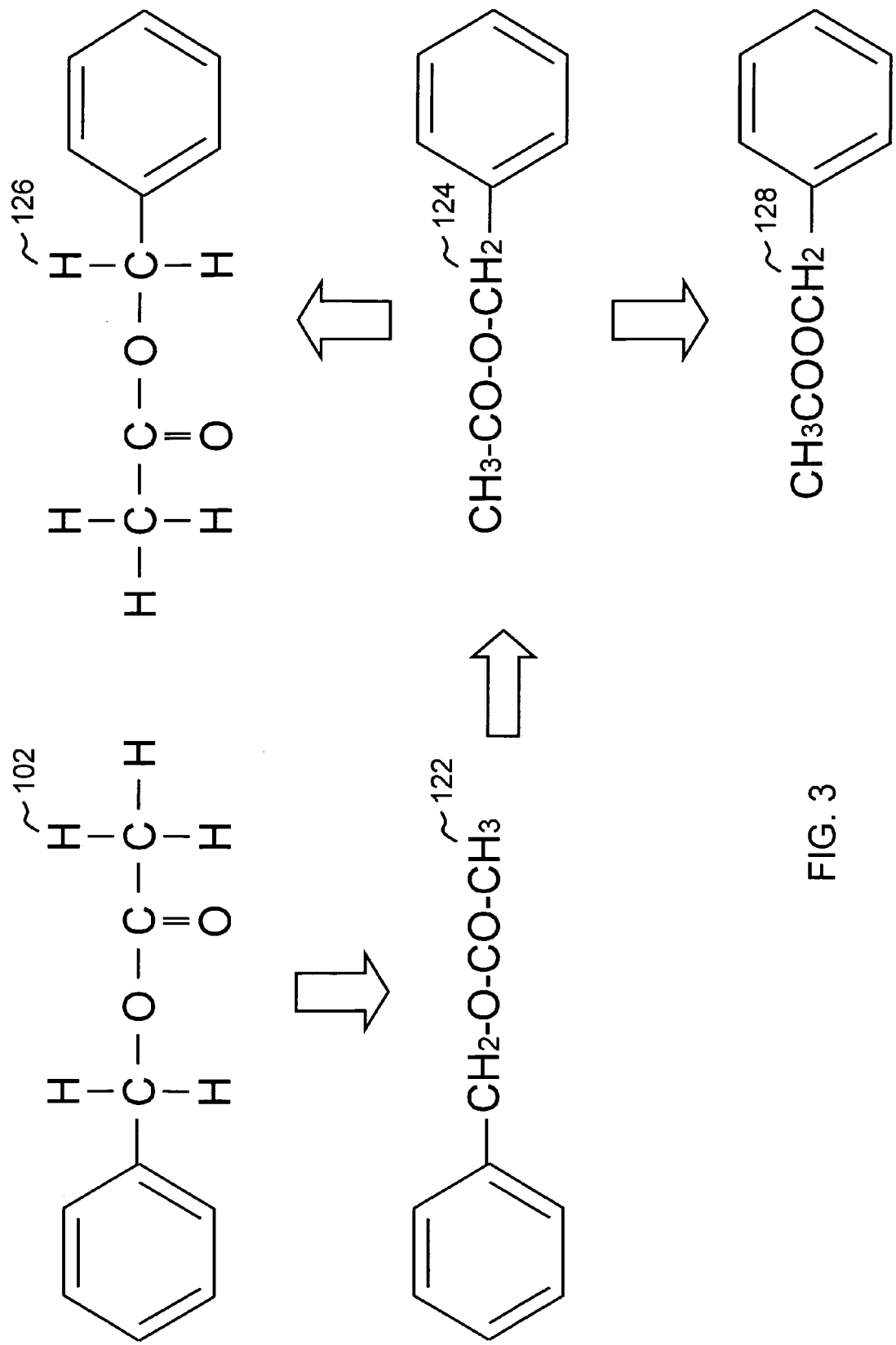
FIG. 3 is a diagram illustrating correspondence between the graphic expression and the character string expression.

FIG. 3 is a diagram illustrating correspondence between the graphic expression and the character string expression. In Structural Formula 122, a portion other than the benzene ring in Structural Formula 102 is divided into a plurality of groups at bonding sites on a main chain (i.e., backbone of the carbon skeleton in the chain structure) and displayed in character string expression. For the sake of comparison, "-" is inserted between the groups. In Structural Formula 124, the alignment of the plurality of groups constituting the character string part in Structural Formula 122 is mirror-reversed. In Structural Formula 126, the character string expression in Structural Formula 124 is switched back to the graphic expression. Structural Formula 126 is a mirror reverse of Structural Formula 102. That is, Structural Formula 124 is an expression that maintains the group patterns while keeping the bonding relationships between elements in Structural Formula 102. In Structural Formula 128, "-" is removed from the character string part in Structural Formula 124. Since Structural Formula 128 is an expression in which group patterns are maintained, it is far easier for the user to understand the structure of the compound represented by Structural Formula 128 than Structural Formula 114.

In typical character string notation, as shown in Structural Formula 106, a plurality of groups are aligned in order assuming that another structure is connected to the left side of the character string. Hereinafter, such a notation will be referred to as "notation directed rightward". On the other hand, in Structural Formula 128, a plurality of groups are aligned in order assuming that another structure is connected to the right side of the character string. Hereinafter, such a notation will be referred to as "notation directed leftward".

Figure 4:
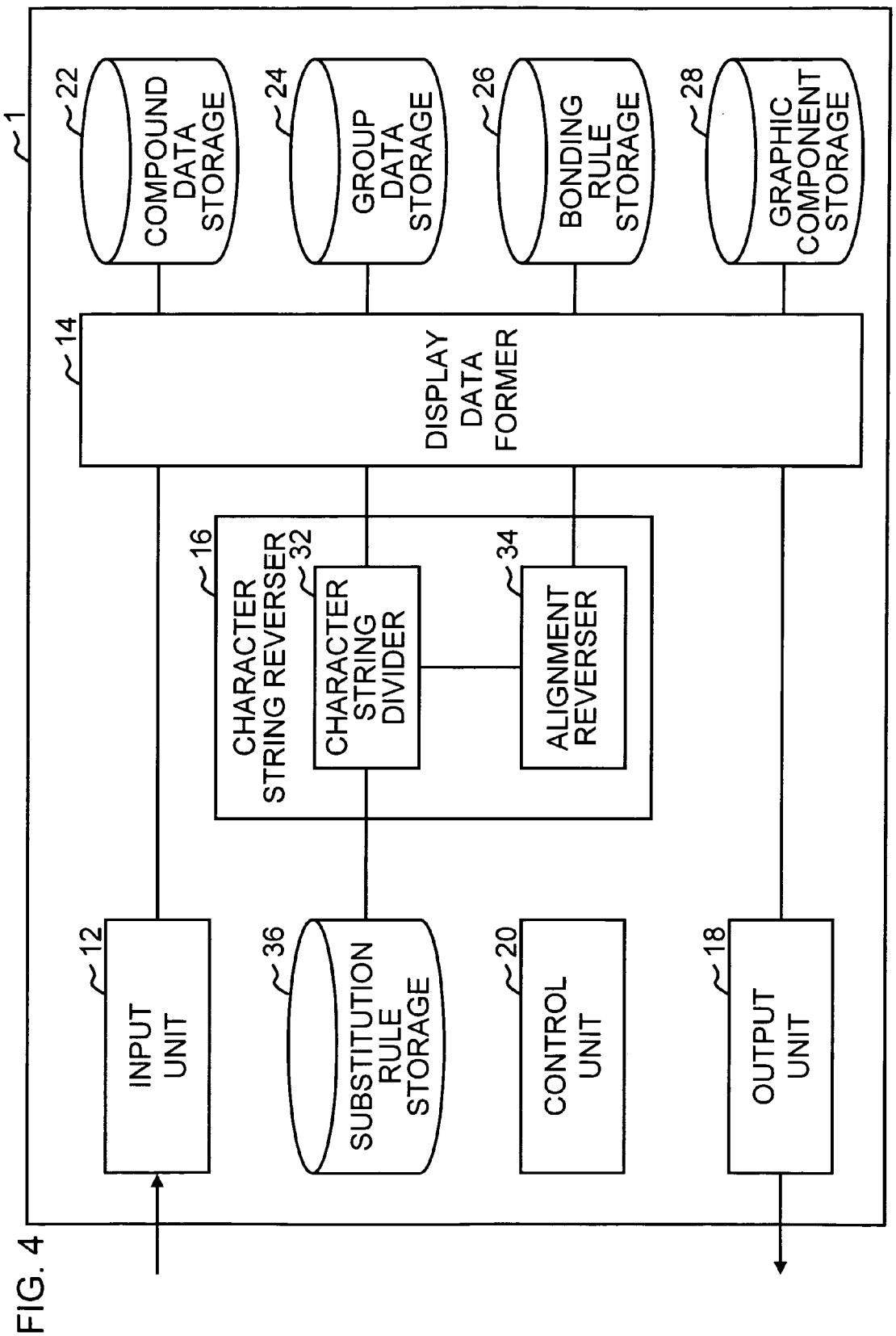
FIG. 4 is a diagram illustrating a system configuration of a structural formula display system according to an embodiment of the present invention.

FIG. 4 is a diagram illustrating a system configuration of a structural formula display system according to an embodiment of the present invention. The structural formula display system 1 includes an input unit 12 for accepting an input operation from the user, a display data former 14 for forming data of a structural formula to be displayed, a character string reverser 16 for mirror-reversing the alignment of the plurality of groups constituting the character string part in the structural formula, an output unit 18 for displaying the structural formula on the basis of display data, a control unit 20 for controlling the entire structural formula display system 1, a compound data storage 22 for storing data on compounds, a group data storage 24 for storing data on groups, a bonding rule storage 26 for storing element bonding rules, a graphic component storage 28 for storing graphic components used when a structural formula is displayed in graphic expression, and a substitution rule storage 36 for storing substitution rules used when a character string in a structural formula is divided. The character string reverser 16 includes a character string divider 32 for dividing a character string into a plurality of groups at one or more bonding sites on a main chain, and an alignment reverser 34 for mirror-reversing the alignment of the plurality of groups.

The input unit 12 accepts an input operation into the structural formula display system 1 from the user. The input operation from the user includes input for designating a structural formula to be displayed and input for changing the structural formula displayed. The input for designating a structural formula to be displayed may be performed in any manner. Examples of the method for the input include selection of a compound from a compound list, input of a composition formula of a compound, selection of a graphic component, and input of an atomic symbol. These methods may be combined. Examples of the change in the structural formula displayed include changes in size of the structural formula and the position to be displayed, changes in the structure in a part of the structural formula, changes in expression in a part of the structural formula from graphic expression to character string expression, changes in expression in a part of the structural formula from character string expression to graphic expression, and changes in the position to be displayed for a part of the structural formula.

The display data former 14 forms data of the structural formula to be displayed on the basis of the input from the user and changes the data of the structural formula to be displayed on the basis of the input from the user. The data of the structural formula may be formed in any manner in response to the method designated by the user. For example, a structural formula stored in advance may be retrieved with respect to a compound selected by the user from the compound list. A structural formula stored in advance may be retrieved on the basis of the composition formula inputted by the user. A structural formula may be estimated on the basis of the composition formula inputted by the user and the bonding rule with respect to elements. A structural formula may be constructed on the basis of the graphic components selected by the user and the atomic symbols inputted by the user. The changes in expression in a part of the structural formula from character string expression to graphic expression or changes in expression in a part of the structural formula from graphic expression to character string expression may be performed in any manner. For example, in the structural formula data of a compound stored in advance, the character string expression and the graphic expression of a target portion may be compared. In the structural formula data of a group stored in advance, the character string expression and the graphic expression may be compared. Conversion between the character string expression and the graphic expression may be performed on the basis of bonding rules.

When a portion of a structural formula is displayed in character string expression and when the display data former 14 determines that the reversal in alignment of the character string expression is required depending on the positional relationship with the other portion of the structural formula, the character string reverser 16 mirror-reverses the alignment of a plurality of groups constituting the character string.

The character string divider 32 divides the character string into a plurality of groups at one or more bonding sites on the main chain in preparation for the reversal in alignment of the character string. Furthermore, the expression of a character string representing each group may be changed so that the user can easily understand the structural formula after the reversal is made.

The alignment reverser 34 mirror-reverses the alignment of the plurality of groups constituting the divided character string.

The output unit 18 displays the structural formula on the basis of the display data and also produces required outputs.

The control unit 20 controls the entire structural formula display system 1. In the structural formula display system 1, all processes other than those carried out by the individual means described above are carried out by the control unit 20.

The compound data storage 22 stores data on various compounds, i.e., a name of compound, a corresponding composition formula, a corresponding structural formula in character string expression, and a corresponding structural formula in graphic expression.

The group data storage 24 stores data on various groups, i.e., name of group, a corresponding composition formula, a corresponding structural formula in character string expression, and a corresponding structural formula in graphic expression.

The bonding rule storage 26 stores bonding rules for bonding various elements together.

The graphic component storage 28 stores various graphic components used for displaying a structural formula in graphic expression.

The substitution rule storage 36 stores substitution rules for substituting characters in a character string in the course of dividing a structural formula.

In the structural formula display system 1 according to the present invention, processes other than the character string reversing process performed in the character string reverser 16 are the same as those in conventional structural formula display systems, and thus descriptions thereof will be omitted.

Figure 5:
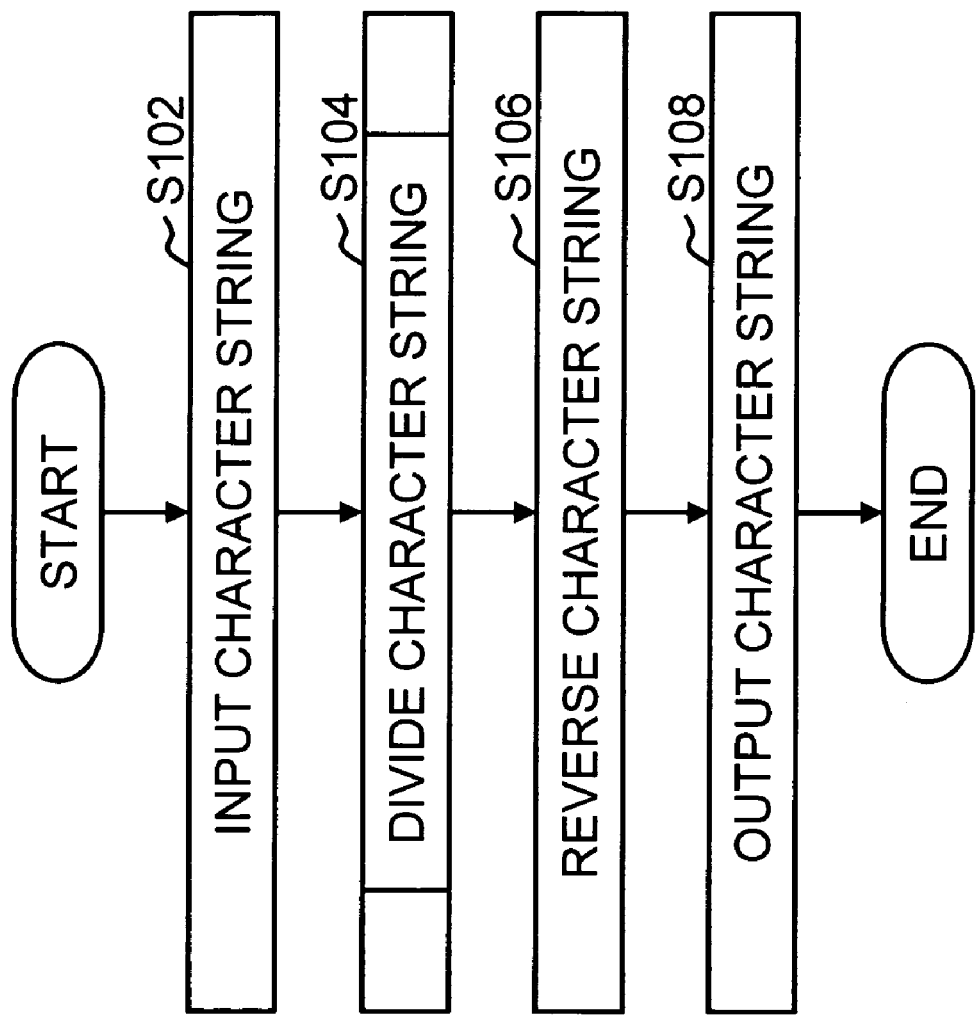
FIG. 5 is a flowchart of the character string reversing process according to an embodiment of the present invention.

FIG. 5 is a flowchart of the character string reversing process according to an embodiment of the present invention. The flow of the character string reversing process according to the embodiment will be described with reference to FIG. 5 in the order of steps S102 to S108.

(Step S102) The character string divider 32 inputs a character string to be subjected to character string reversing process. The character string divider 32 also acquires information on whether the character string is in a notation directed rightward or a notation directed leftward.

(Step S104) The character string divider 32 divides the inputted character string into a plurality of groups at each bonding site on a main chain. The details of the character string dividing process will be described later.

(Step S106) The alignment reverser 34 mirror-reverses the alignment of the groups in the divided character string. In the divided character string, a delimiter is inserted between adjacent groups. The alignment reverser 34 extracts groups from the divided character string on the basis of the delimiters, and rearranges the groups in the character string such that the left-to-right order of alignment of the plurality of groups in the character string is reversed. Resulted character string includes no delimiters.

(Step S108) The alignment reverser 34 outputs the reversed character string.

Figure 6:
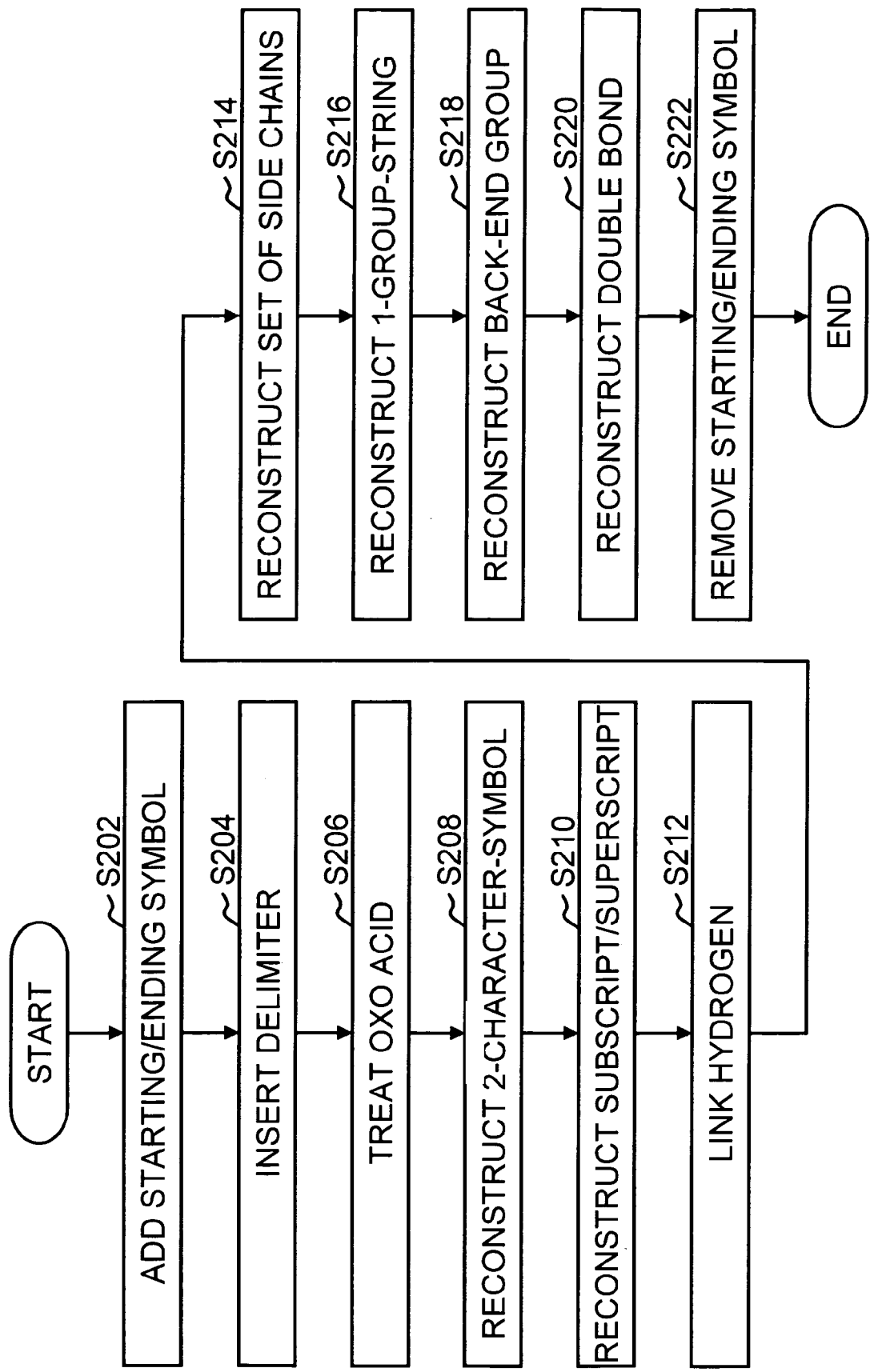
FIG. 6 is a flowchart of the character string dividing process according to an embodiment of the present invention.

FIG. 6 is a flowchart of the character string dividing process according to an embodiment of the present invention. The flow of the character string dividing process according to the embodiment will be described with reference to FIG. 6 in the order of steps S202 to S222. The character string divider 32 according to the embodiment divides a targeted character string (a character string to be divided) into individual characters, and then the disconnected characters are joined together to reconstruct groups. Furthermore, in the process of reconstruction, the alignment of characters in the substring representing each group is changed as needed.

(Step S202) The character string divider 32 adds starting/ending symbols to a targeted character string. In the case of a notation directed rightward, the left edge is defined as the start edge, and the right edge is defined as the end edge. In the case of a notation directed leftward, the right edge is defined as the start edge, and the left edge is defined as the end edge. FIG. 7 is a diagram illustrating examples of addition of starting/ending symbols. The left side of each arrow represents an original targeted character string, and the right side of each arrow represents the targeted character string after addition of starting/ending symbols. In this embodiment, "%" is used as the starting symbol, and "$" is used as the ending symbol. In FIG. 7, Example 202 is in the case of a notation directed rightward, and Example 204 is in the case of a notation directed leftward.

(Step S204) The character string divider 32 inserts a delimiter between adjacent characters constituting the targeted character string. FIG. 8 is a diagram illustrating an example of insertion of delimiters. In this embodiment, "/" is used as the delimiter.

(Step S206) The character string divider 32 changes a notation related to oxo acids contained in the targeted character string in accordance with a predetermined substitution rule. FIG. 9 is a diagram illustrating examples of the substitution rule regarding oxo acids. In FIG. 9, "*" represents any character string, "?" represents any roman letter other than "O", "l" represents any lower-case roman letter, "n" represents a number equal to or larger than 3, and "n̄" represents a number smaller than n by 1. Each substitution rule means that the character string on the left side of the arrow (referred to as a pre-substitution string) should be replaced with the character string on the right side of the arrow (referred to as a post-substitution string). The character string divider 32 replaces a pre-substitution string contained in the targeted character string with a post-substitution string in accordance with any of the rules 212 to 218.

(Step S208) The character string divider 32 reconstructs an atomic symbol consisting of two characters contained in the targeted character string in accordance with a predetermined substitution rule. FIG. 10 is a diagram illustrating an example of the substitution rule for reconstructing an atomic symbol consisting of two characters. In FIG. 10, "l" represents any lower-case roman letter. The character string divider 32 replaces a pre-substitution string contained in the targeted character string with a post-substitution string in accordance with the rule 222.

(Step S210) The character string divider 32 reconstructs a notation regarding a subscript or superscript contained in the targeted character string in accordance with a predetermined substitution rule. FIG. 11 is a diagram illustrating examples of the substitution rule regarding a subscript or superscript. In FIG. 11, "n" represents any number. The rule 224 is a substitution rule regarding a number representing the number of elements. Each of the rules 226 and 228 is a substitution rule regarding a superscript showing the charge. The rule 230 is a substitution rule regarding a number denoting an isotope. The character string divider 32 replaces a pre-substitution string contained in the targeted character string with a post-substitution string in accordance with any of the rules 224 to 230.

(Step S212) The character string divider 32 links hydrogen contained in the targeted character string to another element in accordance with a predetermined substitution rule. FIG. 12 is a diagram illustrating examples of the substitution rule regarding hydrogen. The character string divider 32 replaces a pre-substitution string contained in the targeted character string with a post-substitution string in accordance with the rules 232 and 234.

(Step S214) The character string divider 32 reconstructs a set of side chains contained in the targeted character string in accordance with a predetermined substitution rule. FIG. 13 is a diagram illustrating an example of the substitution rule for reconstructing a set of side chains. In FIG. 13, "(" and ")" correspond to each other, "*" represents any character string, and "*̄" represents a character string obtained by removing delimiters from "*". The character string divider 32 replaces a pre-substitution string contained in the targeted character string with a post-substitution string in accordance with the rule 236.

Figure 14:
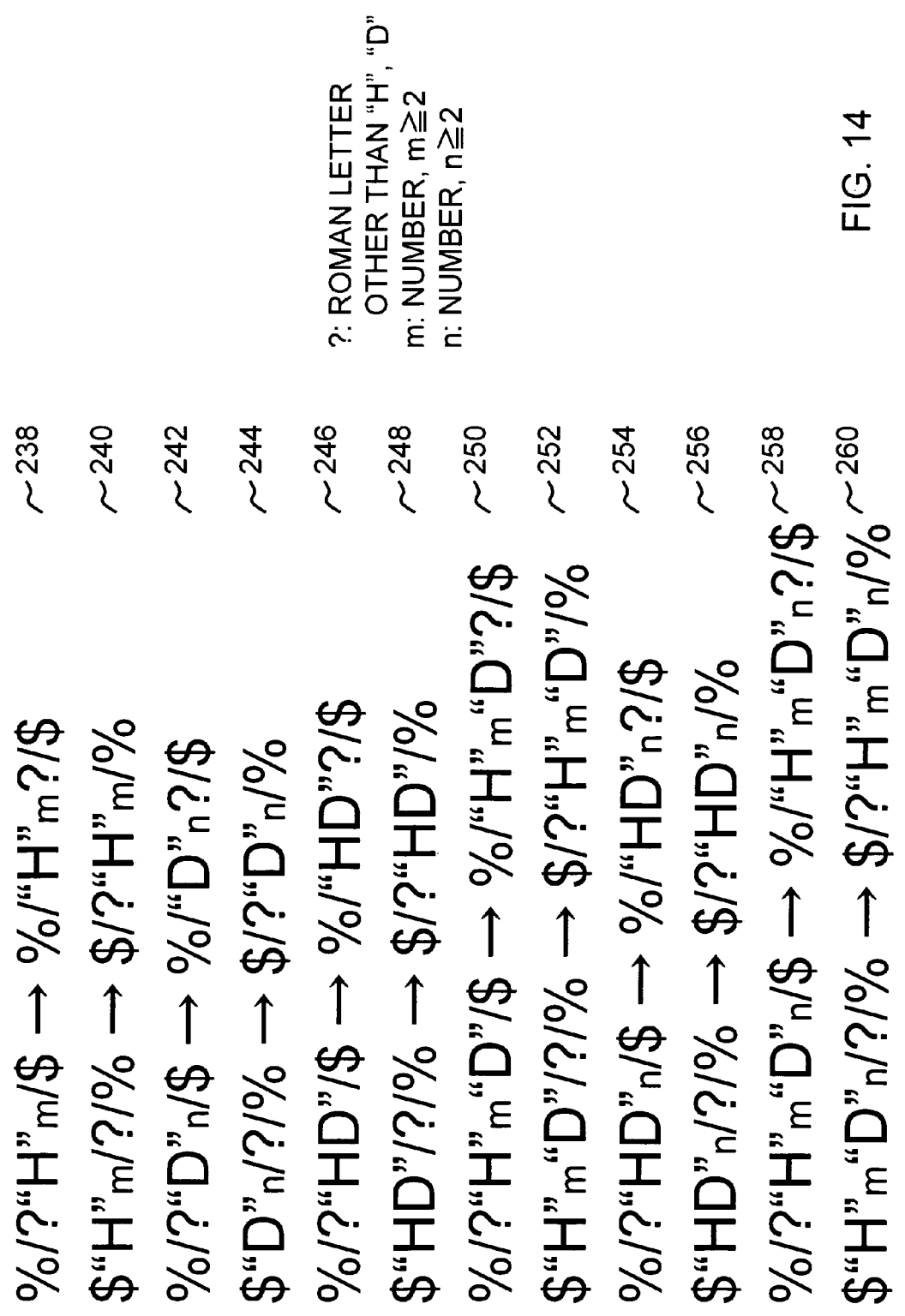

(Step S216) The character string divider 32 reconstructs a character string consisting of one group in accordance with a predetermined substitution rule. The expression of the character string of the group is changed here. FIG. 14 is a diagram illustrating examples of the substitution rule for reconstructing a character string consisting of one group. In FIG. 14, "?" represents an roman letter other than "H" and "D", and each of m and n represents a number equal to or larger than 2. The character string divider 32 replaces a pre-substitution string contained in the targeted character string with a post-substitution string in accordance with any of the rules 238 to 260.

(Step S218) The character string divider 32 reconstructs a back-end group in accordance with a predetermined substitution rule. The expression of the character string of the group is changed here. FIG. 15 is a diagram illustrating examples of the substitution rule for reconstructing a back-end group. The character string divider 32 replaces a pre-substitution string contained in the targeted character string with a post-substitution string in accordance with any of the rules 262 to 280.

(Step S220) The character string divider 32 reconstructs a double bond in a group in accordance with a predetermined substitution rule. FIG. 16 is a diagram illustrating examples of the substitution rule for reconstructing a double bond in a group. The character string divider 32 replaces a pre-substitution string contained in the targeted character string with a post-substitution string in accordance with any of the rules 282 to 292.

(Step S222) The character string divider 32 removes starting/ending symbols from the targeted character string. Delimiters adjacent to the starting/ending symbols are, if any, also removed.

Figure 17:
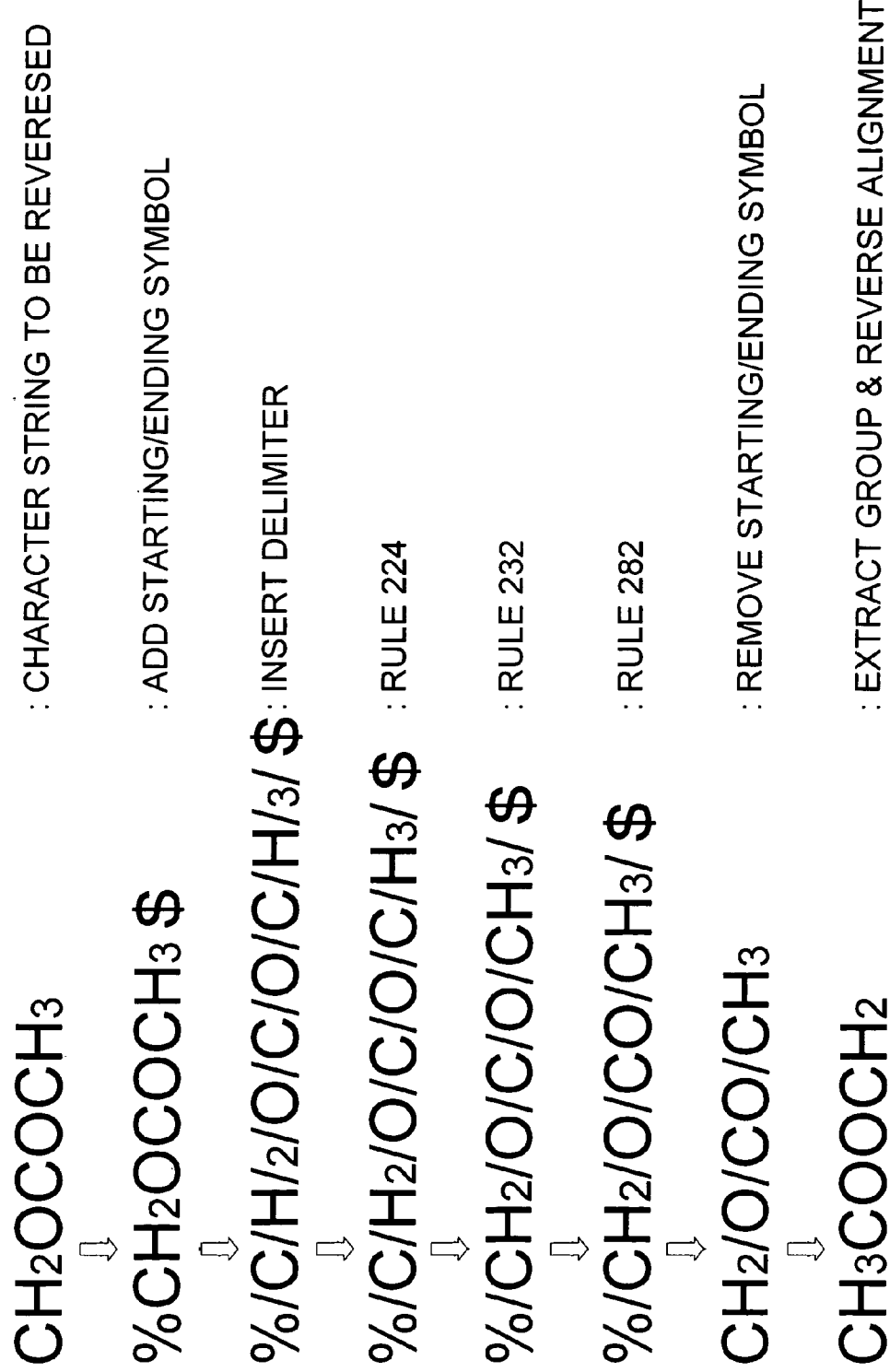
FIG. 17 is a diagram illustrating an example of character string dividing process.

FIG. 17 is a diagram illustrating an example of character string dividing process. In the example shown in FIG. 17, the rules 224, 232, and 282 are applied.

By employing the configuration described above, it is possible to mirror-reverse the alignment of groups constituting a character string part in a structural formula.

In this embodiment, a method is used in which the targeted character string is divided into individual characters, and then the divided characters are joined together and groups are reconstructed on the basis of the substitution rules. However, the method for dividing the character string is not limited thereto. A method may be used in which dividable positions in a character string are determined sequentially. What is essential is that a character string is divided into a plurality of groups at each bonding sites on a main chain.

As described above, according to the present invention, since the alignment of groups constituting a character string can be mirror-reversed, the expression of each group is maintained familiar to the user. Thus, it is possible to provide a structural formula display method in which the structure of the compound can be easily understood by the user even if the alignment of the character string is changed.

Furthermore, the structural formula display system according to any of the embodiments described above can be implemented not only as hardware but also as computer software. For example, when a program which makes a computer execute the functions of the input unit 12, display data former 14, character string divider 32, alignment reverser 34, output unit 18, and control unit 20 shown in FIG. 4 is written, and when the program is allowed to be read in a memory of a computer and executed, a structural formula display system can be implemented.

A program for implementing a structural formula display system according to the embodiment of the present invention may be stored in a portable recording medium 54, such as CD-ROM, CD-RW, DVD-R, DVD-RAM, DVD-RW, or a flexible disk, as shown in FIG. 18. The program may also be stored in a storage device or recording medium 60 such as a hard disk or RAM in a computer system 52, or in another storage device 58 connected via a communication line 56. When the program is executed, the program is loaded and executed on the main memory.

What is claimed is:

1. A hardware system for displaying a structural formula of a compound, said hardware system comprising:
   an input unit for accepting the structural formula;
   a character string divider configured to execute a character string dividing process for dividing a character string corresponding to a part of the structural formula into a plurality of substrings, each of said substrings corresponding to a group derived by dividing the part of the structural formula at each bonding site on a main chain;
   an alignment reverser for reversing an order of alignment of the plurality of substrings in the character string, the alignment reverser reversing only the plurality of substrings derived through the character string dividing process executed by the character string divider; and
   an output unit for displaying the structural formula after the reversal.

2. The hardware system of claim 1, wherein
   the character string divider modifies a substring out of the plurality of substrings.

3. A structural formula display method performed by a hardware system for displaying a structural formula of a compound, said structural formula display method comprising:
   accepting the structural formula;
   dividing, by a character string divider included in the hardware system, a character string corresponding to a part of the structural formula into a plurality of substrings, each of said substrings corresponding to a group derived by dividing the part of the structural formula at each bonding site on a main chain, the character string divider executing a character string dividing process;

reversing an order of alignment of the plurality of substrings in the character string, the hardware system reversing only the plurality of substrings derived through the dividing executed by the character string divider; and displaying the structural formula after the reversal.

4. The structural formula display method of claim 3, wherein a substring out of the plurality of substrings is modified in the operation of dividing a character string.

5. A non-transitory computer-readable storage medium storing a program causing a computer to execute a structural formula display method for displaying a structural formula of a compound, said structural formula display method comprising:

accepting the structural formula;

dividing, in a character string dividing process executed by the computer as a character string divider, a character string corresponding to a part of the structural formula into a plurality of substrings, each of said substrings corresponding to a group derived by dividing the part of the structural formula at each bonding site on a main chain;

reversing an order of alignment of the plurality of substrings in the character string, the computer reversing only the plurality of substrings derived through the character string dividing process executed by the computer as the character string divider; and displaying the structural formula after the reversal.

6. The non-transitory computer-readable storage medium of claim 5, wherein a substring out of the plurality of substrings is modified in the operation of dividing a character string.

* * * * *